US010059965B2

(12) United States Patent
Tsuchida et al.

(10) Patent No.: US 10,059,965 B2
(45) Date of Patent: Aug. 28, 2018

(54) HIGHLY EFFICIENT ETHANOL-FERMENTATIVE YEAST

(71) Applicant: HONDA MOTOR CO., LTD., Tokyo (JP)

(72) Inventors: Yoshiki Tsuchida, Saitama (JP); Ikumi Kurihara, Saitama (JP); Tomohiro Imai, Saitama (JP); Iku Koike, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 15/532,814

(22) PCT Filed: Dec. 5, 2014

(86) PCT No.: PCT/JP2014/082332
§ 371 (c)(1),
(2) Date: Jun. 2, 2017

(87) PCT Pub. No.: WO2016/088275
PCT Pub. Date: Jun. 9, 2016

(65) Prior Publication Data
US 2017/0369906 A1 Dec. 28, 2017

(51) Int. Cl.
| | | |
|---|---|---|
| *C12N 1/14* | (2006.01) | |
| *C12P 7/06* | (2006.01) | |
| *C12R 1/645* | (2006.01) | |
| *C12N 15/01* | (2006.01) | |
| *C12N 15/90* | (2006.01) | |
| *C12N 15/04* | (2006.01) | |
| *C12R 1/84* | (2006.01) | |
| *C12N 1/16* | (2006.01) | |
| *C12N 15/09* | (2006.01) | |

(52) U.S. Cl.
CPC ............... *C12P 7/06* (2013.01); *C12N 15/01* (2013.01); *C12N 15/04* (2013.01); *C12N 15/905* (2013.01); *C12R 1/645* (2013.01); *C12R 1/84* (2013.01); *C12N 1/16* (2013.01); *C12N 15/09* (2013.01)

(58) Field of Classification Search
CPC .............................. C12N 15/81; C12N 15/815
USPC ..................................................... 435/254.2
See application file for complete search history.

(56) References Cited

U.S. PATENT DOCUMENTS

2013/0189788 A1  7/2013  Zhang et al.

FOREIGN PATENT DOCUMENTS

| JP | 2011-024500 | 2/2011 |
| JP | 2011-193788 | 10/2011 |
| JP | 2012-170422 | 9/2012 |
| WO | 2011/065539 | 6/2011 |

OTHER PUBLICATIONS

Han Li-Li et al., "Breeding of Higher Ethanol Fermentation of Xylose Strain with Protoplast Fusion and Mutagenisis", Liquor Making, vol. 35, No. 2, Mar. 2008, pp. 38-41, Sinkiang, China, Listed in International Search Report, English abstract included, 4 pages.
T. Granstrom et al., "Chemostat study of xylitol production by Candida guilliermondii", Appl Microbiol Biotechnol (2001) 55, pp. 36-42, Mar. 7, 2000, listed in International Search Report, English text, 7 pages.
Paul A. Bicho et al., "Induction of Xylose Reductase and Xylitol Dehydrogenase Activities in Pachysolen tannophilus and Pichia stipitis on Mixed Sugars", Applied and Environmental Microbiology, Jan. 1988, vol. 54, No. 1, pp. 50-54, Ontario, Canada, Discussed in specification, English text, 5 pages.
Cesar Fonseca et al., "L-Arabinose metabolism in Candida arabinofermentans PYCC 5603T and Pichia guilliermondii PYCC 3012: influence of sugar and oxygen on product formation", Appl Microbiol Biotechnol (2007), vol. 75, pp. 303-310, Listed in International Search Report, English text, 8 pages.
Viin Zhang et al., "Metabolic Engineering of a Pentose Metabolism Pathway in Ethanologenic Zymomonas mobilis", Science, Jan. 13, 1995, vol. 267, pp. 240-243, Discussed in specification, English text, 6 pages.
International Search Report, dated Mar. 17, 2015, 2 pages.

*Primary Examiner* — Tekchand Saidha
(74) *Attorney, Agent, or Firm* — Rankin, Hill & Clark LLP

(57) ABSTRACT

A highly efficient ethanol-fermentative yeast having high efficiency in ethanol production is provided without introducing a foreign gene. The highly efficient ethanol-fermentative yeast features a fermentative yeast effectively producing ethanol from pentose and hexose and being deposited to NITE Patent Microorganisms Depositary under the accession number NITE BP-01963.

1 Claim, 2 Drawing Sheets
Specification includes a Sequence Listing.

HIGHLY EFFICIENT ETHANOL-FERMENTATIVE YEAST

TECHNICAL FIELD

The present invention relates to a yeast for fermenting a saccharified solution in bioethanol production using lignocellulosic biomass.

In particular, the present invention relates to a yeast capable of effectively producing ethanol from pentose (which may be, hereinafter, referred to as C5 sugar) and hexose (which may be, hereinafter, referred to as C6 sugar) in bioethanol production using lignocellulosic biomass.

BACKGROUND ART

Bioethanol is expected to be a renewable resource that is produced by biomass. Moreover, since carbon dioxide that is produced by combustion of bioethanol is carbon neutral, increased use of bioethanol is considered to suppress increase of carbon dioxide, which is a main cause of the global warming.

Bioethanol is obtained by fermenting biomass and distilling and purifying ethanol. It is necessary to produce much alcohol from saccharified solutions for increasing the yield of bioethanol. Since the yeasts generally used in the process of bioethanol production cannot convert pentose such as xylose and arabinose into alcohol, only hexose has been used as raw materials for fermentation.

Typical biomass is reported to contain 35-45% of cellulose, 25-40% of hemicellulose, and 15-30% of lignin, though the contents vary according to raw materials. Therefore, use of hemicellulose, which mainly contains the pentose xylose, but not only cellulose, which is a polymer of hexose, as a substrate should lead to effective ethanol production.

Xylose is reported to be the second abundant sugar in biomass next to glucose and it is an important object in bioethanol production to use pentose effectively.

Techniques for using xylose, even at a little amount, by imparting the ability to utilize xylose by genetic recombination, using microorganism that produces ethanol from xylose, or the like have been so far disclosed.

Patent Literature 1 discloses an invention involving converting xylose (C5 sugar) into xylulose by introducing a gene having the xylose transporter activity into a host cell to incorporate it in the pentose phosphate pathway of the glycolysis and use it for fermentation.

Patent Literature 2 discloses a technique for producing alcohol with yeast provided with an arabinose transporter. This involves incorporation of arabinose (C5 sugar) via arabitol and xylulose in the pentose phosphate pathway in the glycolysis to use it for fermentation, similar to the invention of Patent Literature 1.

Non Patent Literature 1 discloses provision of xylose utilization ability by incorporating a xylose utilization gene derived from *Escherichia* coli in *Zymomonas*.

Non Patent Literature 2 describes production of ethanol from xylose by yeast in the genus *Pichia*.

CITATION LIST

Patent Literature

Patent Literature 1:
 Japanese Patent Laid-Open No. 2012-170422
Patent Literature 2:
 U.S. Patent Application Publication No. 2013/189788

Non Patent Literature

Non Patent Literature 1:
 Zhang, M., et al., Science, 1995. Vol. 267, pp. 240-243.
Non Patent Literature 2:
 Bicho, P. A., et al., Appl. Environ. Microbiol., 1988, Vol. 54, pp. 50-54.

SUMMARY OF INVENTION

Technical Problem

However, the invention of Patent Literature 1 involves introducing a protein having the xylose transporter activity derived from *Candida guilliermondii* into *Saccharomyces cerevisiae* as a host. Accordingly, a foreign gene would be introduced. The invention of Patent Literature 2 is also an invention involving introduction of a gene from a species different from the host, although the transporter gene is different.

The technique described in Non Patent Literature 1 also involves introduction of a xylose utilization gene. The technical concept thereof is different from Patent Literature 1 and 2 described above, but they are similar in that a foreign gene is introduced.

Therefore, any of the techniques described in Patent Literature 1 and 2 and Non Patent Literature 1 requires adopting a containment measure to comply with so-called the Cartagena Act enforced in Japan to implement "the Cartagena Protocol on Biosafety to the Convention on Biological Diversity" adopted in the United Nations. Accordingly, producing ethanol with such a yeast is disadvantageous in cost because it requires facilities to guarantee biosafety.

Moreover, use of yeast in the genus *Pichia* by the technique described in Non Patent Literature 2 does not result in a much higher efficiency of ethanol production because of the low xylose availability in the wild-type *Pichia* yeast.

An object of the present invention is to obtain a high efficient ethanol-fermentative yeast having a highly efficient ethanol production without introducing a foreign gene.

Solution to Problem

To achieve the aforementioned object, the highly efficient ethanol-fermentative yeast according to the present invention features a fermentative yeast effectively producing ethanol from pentose and hexose, wherein the fermentative yeast is a yeast in which self-cloned transaldolase gene, alcohol dehydrogenase gene, and pyruvate decarboxylase gene are introduced in a highly efficient ethanol-fermentative yeast deposited to NITE Patent Microorganisms Depositary under the accession number NITE BP-01962 and wherein the fermentative yeast is deposited to NITE Patent Microorganisms Depositary under the accession number NITE BP-01963.

The wild-type *Meyerozyma guilliermondii* has a xylose utilization ability in addition to glucose utilization ability. However, it does not comprise sufficient ability to utilize xylose for the bioethanol production. In contrast, the highly efficient ethanol-fermentative yeast according to the present invention (which may be, hereinafter, also referred to as strain BP-01963) is a yeast in which self-cloned transaldolase gene, alcohol dehydrogenase gene, and pyruvate decarboxylase gene are introduced into a fermentative yeast (accession number: NITE BP-01962, which may be, hereinafter, also referred to as strain BP-01962) obtained by performing strain improvement of a parent strain of *Meyerozyma guilliermondii* and selecting a yeast having a high xylose utilization efficiency.

The aforementioned transaldolase, alcohol dehydrogenase, and pyruvate decarboxylase genes are all from of *Meyerozyma guilliermondii*.

The aforementioned transaldolase gene is an enzyme in the pentose phosphate pathway and the enhancement of the gene is predicted to facilitate the utilization of xylose. The aforementioned alcohol dehydrogenase gene produces ethanol from acetaldehyde. The pyruvate decarboxylase gene decarboxylates pyruvic acid and produces acetaldehyde and $CO_2$.

As a result, the highly efficient ethanol-fermentative yeast according to the present invention can have ethanol production efficiency higher than the parent strain without introducing a foreign gene.

DESCRIPTION OF EMBODIMENTS

Figure 1:
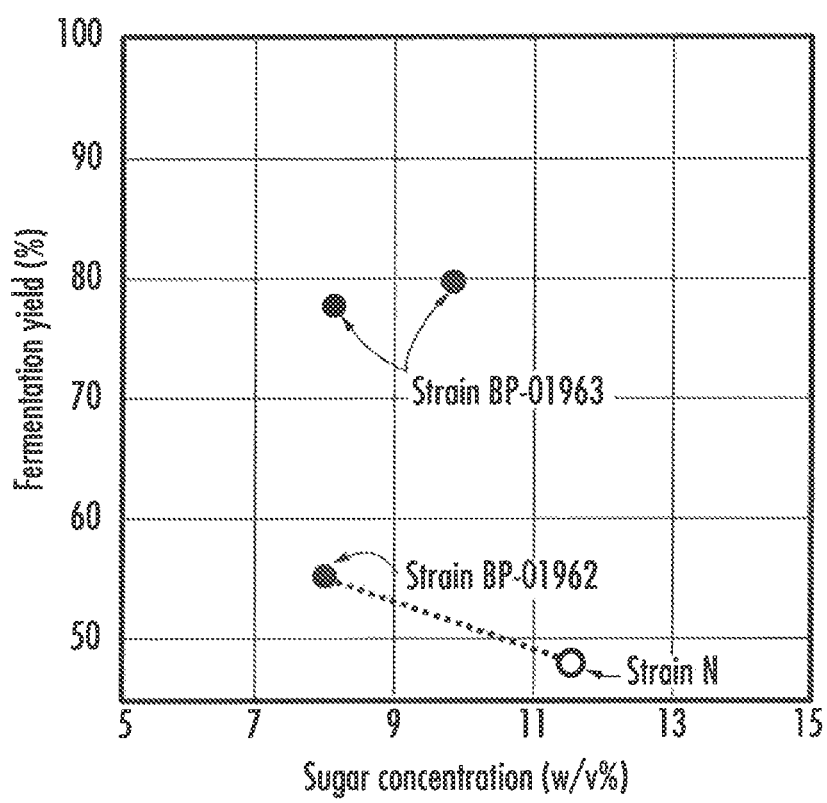
FIG. 1 is a graph illustrating the relation between the sugar concentration and the fermentation yield of the strains BP-01963, BP-01962, and N in an enzymatically saccharified liquid derived from corn stover treated with dilute sulphuric acid.

Next, embodiment of the present invention is further described in detail, referring to the accompanying drawings.

The wild type of the Ascomycete yeast *Meyerozyma guilliermondii* includes xylose utilization ability in addition to glucose utilization ability. However, the ability thereof to utilize xylose is not considered to be sufficient for the bioethanol production. Therefore a highly efficient ethanol-fermentative yeast according to the embodiment is a yeast in which a self-cloned transaldolase gene (hereinafter, referred to as TAL gene), a self-cloned alcohol dehydrogenase gene (hereinafter, referred to as ADH gene), and a self-cloned pyruvate decarboxylase gene (hereinafter, referred to as PDC gene) were introduced into a fermentative yeast (accession number: NITE BP-01962) obtained by performing habituation using the strain N of the Ascomycete yeast *Meyerozyma guilliermondii* as a parent strain in culture in a medium in which a mutagen is added to an enzymatically saccharified liquid derived from rice straw treated with ammonia and selecting a yeast growing in the medium.

Examples of the aforementioned enzymatically saccharified liquid derived from rice straw treated with ammonia that can be used include the one obtained as follows. Rice straw from Kumagaya-shi, Saitama, Japan was pretreated by immersing it in an equal amount of a 25 mass % ammonium solution at a temperature of 80° C. for 3 hours and then ammonia was evaporated. Next, after pH adjustment, a saccharification enzyme (manufactured by Meiji Seika Pharma Co., trade name: Acremonium cellulase) was added to the pretreated rice straw and enzymatic saccharification was conducted with maintaining temperature at 50° C. for 72 hours to obtain a slurry containing an enzymatically saccharified liquid. Then, solid-liquid separation of the slurry was conducted by filter-pressing to collect a liquid as the aforementioned enzymatically saccharified liquid derived from rice straw treated with ammonia. The enzymatically saccharified liquid derived from rice straw treated with ammonia contains, for example, 3-15 mass % of glucose and 1-10 mass % of xylose.

Examples of the mutagen that can be used include ethylating agents such as N-ethyl-N-nitrosourea (ENU) and ethyl methanesulfonate (EMS), base analogs such as 5-bromo-2'-deoxyuridine (BrdU), and nitroso compounds such as nitroamine and nitrosoguanidine.

The strain BP-01962 is a mutant strain obtained by habituation of the aforementioned parent strain in culture in the aforementioned medium in which a mutagen is added to an enzymatically saccharified liquid derived from rice straw treated with ammonia and repeated selection of yeasts growing in the medium. Therefore, the strain BP-01962 has improved xylose utilization and ethanol fermentation performance in comparison with the wild type strain or the strain N of *Meyerozyma guilliermondii* without introducing a foreign gene.

The highly efficient ethanol-fermentative yeast according to the embodiment in which the self-cloned TAL, ADH, and PDC genes are introduced into the strain BP-01962 has been deposited to NITE Patent Microorganisms Depositary (#122, 2-5-8 Kazusakamatari, Kisarazu-shi, Chiba 292-0818, Japan), National Institute of Technology and Evaluation (Independent Administrative Institution) by the present applicant. The accession date is Nov. 19, 2014 and the accession number is NITE BP-01963.

The TAL, ADH, and PDC genes are all from *Meyerozyma guilliermondii*. Therefore, the introduction of these self-cloned genes into the strain BP-01962 involves no introduction of a foreign gene.

As a result, the strain BP-01963 has further improved xylose utilization and ethanol fermentation performance in comparison with the strain BP-01962 or the strain N without introducing a foreign gene.

The introduction of self-cloned TAL, ADH, and PDC genes into the strain BP-01963 can be conducted, for example, as follows.

Amplify the gene to be introduced and a terminator region thereof (hereinafter, referred to as gene+terminator region) by PCR. Amplify by PCR the promoter region to be used for the introduction. These should be both amplified by PCR from the chromosomes of the strain of *Meyerozyma guilliermondii* used in the present invention.

Clone the DNA fragments amplified by PCR into a commercially available vector for *Escherichia coli* by infusion in the order of promoter, gene+terminator region. Transform *Escherichia coli* with the cloned vector and amplify the vector. Obtain DNA fragments for homologous recombination by cutting out the promoter and gene+terminator region from the amplified vector with restriction enzymes or amplifying the promoter and gene+terminator region from the amplified vector by PCR.

Homologous recombination of the strain with the obtained DNA fragments was performed to obtain a desired strain. Electroporation was used for the homologous recombination. Genetic introduction in this manner allows introduction of multiple copies into the chromosomes and therefore enhancement of the activity of the introduced enzyme.

As a DNA fragment for the homologous recombination, for example, the promoter of xylose reductase, transaldolase+terminator may be preferably used because transaldolase is considered to work efficiently when using the promoter of xylose reductase that functions in the xylose utilization.

Specifically, the xylose reductase promoter was amplified with the following primers of SEQ ID NO: 1 and SEQ ID NO: 2 and the transaldolase gene and the terminator region are amplified with the following primers of SEQ ID NOs: 3 and 4.

```
SEQ ID NO: 1:
AAGGCTTGGGAACTTTCTTT

SEQ ID NO: 2:
AGCAATTGATGATTAATTTT

SEQ ID NO: 3:
ATGACCAATTCTCTTGAACA

SEQ ID NO: 4:
AAATTGTGCCGTGTCAAACT
```

Moreover, the promoter of GAPDH and alcohol dehydrogenase+terminator may be preferably used. Since the GAPDH is a strong promoter that functions in glycolysis, it is considered to be an efficient promoter for use as a promoter of alcohol dehydrogenase, which is an enzyme in glycolysis. Alcohol dehydrogenase produces NAD+ when it is NADH-dependent as well as serves to convert acetaldehyde into ethanol. Therefore, it serves to enhance the effect of NAD+-dependent xylitol dehydrogenase.

Specifically, the GAPDH promoter was amplified with the primers of the following SEQ ID NO: 5 and SEQ ID NO: 6 and the alcohol dehydrogenase gene and terminator region is amplified with the primers of the following SEQ ID NOs: 7 and 8.

```
SEQ ID NO: 5:
GTTGTAGCGGAGGCTCAATT

SEQ ID NO: 6:
TGTATAATTTAAATGTGGGT

SEQ ID NO: 7:
ATGTCAATTCCAGAATCCAT

SEQ ID NO: 8:
CACCTTGGCTGGAAGTGCTG
```

The PDC gene was enhanced by replacing the promoter of the PDC gene with the promoter of GAPDH. The replacement was performed by the homologous recombination with a DNA fragment obtained by introducing the promoter of GAPDH amplified with the primers of SEQ ID NO: 5 and SEQ ID NO: 6 between the sequences set forth in SEQ ID NO: 9 and SEQ ID NO: 10. The sequence set forth in SEQ ID NO: 9 corresponds to the terminal end of the PDC gene promoter and the sequence set forth in SEQ ID NO: 10 corresponds to the starting end of the PDC gene.

```
SEQ ID NO: 9:
AGATTGCTGCAAAAATCATC

SEQ ID NO: 10:
ATGACAGAAATTACTTTGGG
```

Moreover, while the strains obtained by this method comprise an introduced gene, they belong to a category to be treated as a non-modified yeast under the Cartagena Act because it is self-cloned.

Next, the fermentation yields of the strain BP-01963 and the strains BP-1962 and N were compared using an enzymatically saccharified liquid derived from corn stover treated with dilute sulphuric acid.

The enzymatically saccharified liquid derived from corn stover treated with dilute sulphuric acid used was obtained as follows. At first, corn stover from Iowa, the United States was pretreated by immersing it in 3.7 mass % sulfuric acid of twice the volume of the corn stover at temperature of 170° C. for 10 minutes and then returning the temperature to room temperature. Next, to the pretreated corn stover, an NaOH aqueous solution was added to adjust pH thereof to pH 4 and then a saccharification enzyme (manufactured by Meiji Seika Pharma Co., Ltd., trade name: Acremonium cellulase) was added and enzymatic saccharification was conducted with maintaining temperature at 50° C. for 72 hours to obtain a slurry containing an enzymatically saccharified liquid. Next, solid-liquid separation of the slurry was conducted by centrifugation and pH of the collected liquid was adjusted to pH 6 with an NaOH aqueous solution, the resultant liquid was used as the aforementioned enzymatically saccharified liquid derived from corn stover treated with dilute sulphuric acid. The enzymatically saccharified liquid derived from corn stover treated with dilute sulphuric acid comprises, for example, 3-15 mass % of glucose and 1-10 mass % of xylose.

Next, an enzymatically saccharified liquid derived from corn stover treated with 15 mass % dilute sulphuric acid was used as a medium. A liquid culture of the strain BP-01963 was added to the medium to an $OD_{600}$ of 2.0 and cultured at a temperature of 30° C. for 100 hours. The enzymatically saccharified liquid derived from corn stover treated with dilute sulphuric acid contained 45 g/L of glucose and 38 g/L of xylose and pH thereof was pH 6. After the culture, the medium was collected and the concentration of ethanol was measured by GC-FID (manufactured by GL Sciences Inc., trade name: GC390B) and the fermentation yield was calculated by the following equation (1). The result is shown in FIG. 1.

$$\text{Fermentation yield} = \text{produced ethanol concentration} / \frac{(\text{glucose concentration} + \text{xylose concentration})}{0.5114} \quad (1)$$

(The Glucose Concentration and the Xylose Concentration are the Initial Concentrations Before the Onset of Culture)

Next, an enzymatically saccharified liquid derived from corn stover treated with 20 mass % dilute sulphuric acid was used as a medium. A liquid culture of the strain BP-01962 was added to the medium to an $OD_{600}$ of 0.5 and cultured at a temperature of 30° C. for 100 hours. The enzymatically saccharified liquid derived from corn stover treated with dilute sulphuric acid contained 64 g/L of glucose and 48 g/L of xylose and pH thereof was pH 6. After the culture, the medium was collected and the concentration of ethanol was measured by GC-FID (manufactured by GL Sciences Inc., trade name: GC390B) and the fermentation yield was calculated by the equation (1). The result is shown in FIG. 1.

Next, an enzymatically saccharified liquid derived from corn stover treated with 26 mass % dilute sulphuric acid was used as a medium. A liquid culture of the strain N of *Meyerozyma guilliermondii* was added to the medium to an $OD_{600}$ of 0.5 and cultured at a temperature of 30° C. for 100 hours. The enzymatically saccharified liquid derived from corn stover treated with dilute sulphuric acid contained 64 g/L of glucose and 48 g/L of xylose and pH thereof was pH 6. After the culture, the medium was collected and the concentration of ethanol was measured by GC-FID (manufactured by GL Sciences Inc., trade name: GC390B) and the fermentation yield was calculated by the equation (1). The result is shown in FIG. 1.

From FIG. 1, it is apparent that the strain BP-01963 comprises the ethanol fermentation performance superior to the strains BP-01962 and N with the lower concentration of the enzymatically saccharified liquid derived from corn stover treated with dilute sulphuric acid than that used for the strain N.

Next, an enzymatically saccharified liquid derived from rice straw treated with 26 mass % ammonia was used as a medium. A liquid culture of the strain BP-01963 was added to the medium to an $OD_{600}$ of 2.0 and cultured at a temperature of 30° C. for 120 hours. The enzymatically saccharified liquid derived from rice straw treated with ammonia contained 73.8 g/L of glucose and 28.3 g/L of xylose and pH thereof was pH 6. The medium was collected at predetermined time points and the concentration of xylose was measured by HPLC (manufactured by Tosoh Corporation, trade name: LC-8020) and the concentration of ethanol by GC-FID (manufactured by GL Sciences Inc., trade name: GC390B). The result is shown in FIG. 2.

Figure 2:
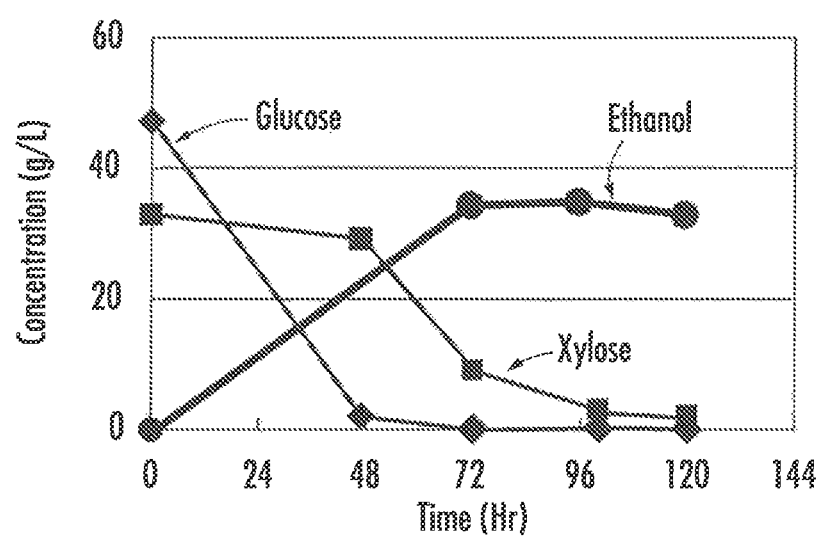
FIG. 2 is a graph illustrating change over time in amount of glucose and xylose digestion and ethanol production by the strain BP-01963 in an enzymatically saccharified liquid derived from rice straw treated with ammonia.

From FIG. 2, it can be seen that the total amount of glucose and xylose is digested 120 hours after the onset of culturing and the ethanol concentration becomes higher over culture time. Also, since the glucose concentration becomes almost zero by 48 hours after the onset of culturing, but the xylose concentration decreases even after that and the ethanol concentration continues increasing, it is apparent that the strain BP-01963 conducts ethanol fermentation using xylose as a substrate after the total amount of glucose is digested.

REFERENCE SIGNS LIST

No reference sign.

---

The invention claimed is:

1. A highly efficient ethanol-fermentative yeast, the fermentative yeast effectively producing ethanol from pentose and hexose, wherein the fermentative yeast is a yeast in which self-cloned transaldolase gene, alcohol dehydrogenase gene, and pyruvate decarboxylase gene are introduced into a highly efficient ethanol-fermentative yeast deposited to NITE Patent Microorganisms Depositary under the accession number NITE BP-01962; and wherein the fermentative yeast is deposited to NITE Patent Microorganisms Depositary under the accession number NITE BP-01963.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Meyerozyma guilliermondii

<400> SEQUENCE: 1
aaggcttggg aactttcttt                                           20

<210> SEQ ID NO 2
<211> LENGTH: 20
<212> TYPE: DNA
<213> ORGANISM: Meyerozyma guilliermondii

<400> SEQUENCE: 2
agcaattgat gattaatttt                                           20

<210> SEQ ID NO 3
<211> LENGTH: 20
<212> TYPE: DNA
<213> ORGANISM: Meyerozyma guilliermondii

<400> SEQUENCE: 3
atgaccaatt ctcttgaaca                                           20

<210> SEQ ID NO 4
<211> LENGTH: 20
<212> TYPE: DNA
<213> ORGANISM: Meyerozyma guilliermondii

<400> SEQUENCE: 4
aaattgtgcc gtgtcaaact                                           20

<210> SEQ ID NO 5
<211> LENGTH: 20
<212> TYPE: DNA
<213> ORGANISM: Meyerozyma guilliermondii

<400> SEQUENCE: 5
gttgtagcgg aggctcaatt                                           20

<210> SEQ ID NO 6
<211> LENGTH: 20
<212> TYPE: DNA
<213> ORGANISM: Meyerozyma guilliermondii

```
<400> SEQUENCE: 6
tgtataattt aaatgtgggt                                                    20

<210> SEQ ID NO 7
<211> LENGTH: 20
<212> TYPE: DNA
<213> ORGANISM: Meyerozyma guilliermondii

<400> SEQUENCE: 7
atgtcaattc cagaatccat                                                    20

<210> SEQ ID NO 8
<211> LENGTH: 20
<212> TYPE: DNA
<213> ORGANISM: Meyerozyma guilliermondii

<400> SEQUENCE: 8
caccttggct ggaagtgctg                                                    20

<210> SEQ ID NO 9
<211> LENGTH: 20
<212> TYPE: DNA
<213> ORGANISM: Meyerozyma guilliermondii

<400> SEQUENCE: 9
agattgctgc aaaaatcatc                                                    20

<210> SEQ ID NO 10
<211> LENGTH: 20
<212> TYPE: DNA
<213> ORGANISM: Meyerozyma guilliermondii

<400> SEQUENCE: 10
atgacagaaa ttactttggg                                                    20
```